US005705661A

United States Patent [19]

Iwakura et al.

[11] Patent Number: 5,705,661
[45] Date of Patent: Jan. 6, 1998

[54] CATALYST FOR PRODUCTION OF ETHYLENE OXIDE

[75] Inventors: Tomoatsu Iwakura; Takako Imamoto; Katsumi Nakashiro, all of Ibaraki, Japan

[73] Assignee: Mitsubishi Chemical Corporation, Tokyo, Japan

[21] Appl. No.: 716,890

[22] Filed: Sep. 20, 1996

[30] Foreign Application Priority Data

Sep. 25, 1995 [JP] Japan .................... 7-246055

[51] Int. Cl.$^6$ .................................. C07D 301/10
[52] U.S. Cl. .............................. 549/536; 502/347
[58] Field of Search ....................... 502/347; 549/536

[56] References Cited

U.S. PATENT DOCUMENTS

| | | | |
|---|---|---|---|
| 4,168,247 | 9/1979 | Hayden et al. | 252/476 |
| 4,212,772 | 7/1980 | Mross et al. | 252/476 |
| 4,414,135 | 11/1983 | Nojiri et al. | 502/224 |
| 4,415,476 | 11/1983 | Ayame et al. | 502/224 |
| 4,642,360 | 2/1987 | Nojiri et al. | 549/534 |
| 4,690,913 | 9/1987 | Nojiri et al. | 502/340 |
| 4,746,749 | 5/1988 | Nojiri et al. | 556/114 |
| 4,786,624 | 11/1988 | Nojiri et al. | 502/226 |
| 4,916,243 | 4/1990 | Bhasin et al. | 549/534 |
| 4,939,114 | 7/1990 | Nojiri et al. | 502/348 |
| 5,502,020 | 3/1996 | Iwakura et al. | 502/317 |

FOREIGN PATENT DOCUMENTS

| | | |
|---|---|---|
| 0 501 317 | 9/1992 | European Pat. Off. . |
| 1 413 251 | 11/1975 | United Kingdom . |
| 1 601 635 | 11/1981 | United Kingdom . |

*Primary Examiner*—C. Warren Ivy
*Assistant Examiner*—Garth M. Dahlen
*Attorney, Agent, or Firm*—Wenderoth, Lind & Ponack

[57] ABSTRACT

A catalyst for oxidizing ethylene and producing ethylene oxide, said catalyst being prepared by pretreating a porous carrier with a solution containing a lithium compound and a cesium compound, thereafter, impregnating a solution containing a silver compound and a cesium compound in the pretreated porous carrier and then heat-treating the impregnated porous carrier.

The use of the catalyst of this invention provides high selectivity in the production of ethylene oxide by the vapor contact oxidation of ethylene.

14 Claims, No Drawings

CATALYST FOR PRODUCTION OF ETHYLENE OXIDE

BACKGROUND OF THE INVENTION

1. Field of the Invention

This invention relates to an improved catalyst for the production of ethylene oxide which is used to produce ethylene oxide by the vapor contact oxidation of ethylene with molecular oxygen, and to a process for producing the catalyst.

Ethylene oxide is suited for the production of nonionic surfactants by being subjected to addition polymerization with active hydrogen compounds, and is also employed as material for polyester- or polyurethane-based high polymers, antifreeze solutions for engines, etc. by being added to water to produce ethylene glycol.

2. Description of the Related Art

The catalyst used for producing ethylene oxide on an industrial scale by the vapor contact oxidation of ethylene with molecular oxygen is a silver catalyst. In order to efficiently produce ethylene oxide, there is a strong demand for an improvement in the silver catalyst, i.e., for highly selective and long-life catalysts. While various methods have been proposed in the past to that end, these methods are primarily concerned with a combination of silver as a main active component with alkaline metal, etc. as a reaction accelerator, an optimization of the mixture ratio, and improvements in carriers on which those components are to be deposited.

GB 1413251 A, for example, describes that high selectivity is achieved by a catalyst in which potassium, rubidium and/or cesium in a specific amount is deposited along with silver on a porous carrier. U.S. Pat. No. 4,212,772 describes that a catalyst containing silver and sodium, potassium, rubidium or cesium in a specific amount can improve the degree of activity and selectivity. Also, U.S. Pat. No. 4,168,247 describes the effect obtained by a combination of two or more alkaline metals selected from among sodium, potassium, rubidium and cesium.

Further, combined use of cesium and lithium among alkaline metals as reaction accelerators is also known. GB 1601635 A, U.S. Pat. No. 4,916,243, etc., disclose catalysts each of which is impregnated with a cesium component and a lithium component at the same time as silver. In addition, EP 501317 A1 describes that when alkaline metals are to be impregnated in a porous carrier having specific properties, a process of impregnating the alkaline metals at the same time as silver, or a process of impregnating a cesium component, in particular, after deposition of silver on the carrier is preferable as a method for improving the performance of the catalyst.

In short, catalysts for the production of ethylene oxide are under situations as follows. While various proposals have been made even for just catalysts wherein alkaline metal is employed as a reaction accelerator, any catalysts cannot be said as reaching a sufficiently satisfactory level. Endeavors to improve the performance of catalysts are being continued increasingly.

SUMMARY OF THE INVENTION

An object of this invention is to provide a catalyst for the production of ethylene oxide which shows higher selectivity and better activity than conventional catalysts, and has long life.

As a result of conducting intensive studies with a view to achieve the above object, the inventors have accomplished this invention based on the finding that high selectivity for ethylene oxide can be obtained by using a catalyst wherein silver and cesium are deposited on a porous carrier which has been pretreated by lithium and cesium.

Specifically, this invention resides in a catalyst used for oxidizing ethylene and producing ethylene oxide, which is prepared by pretreating a porous carrier with a lithium compound and a cesium compound, thereafter, impregnating a silver compound and a cesium compound in the pretreated porous carrier and then heat-treating the impregnated porous carrier.

DESCRIPTION OF THE PREFERRED EMBODIMENTS

The catalyst of this invention will be described hereunder in detail.

Porous Carrier

The catalyst of this invention is a catalyst in which silver is deposited as a catalyst main component on a porous carrier. The porous carrier is made of a porous refractory such as alumina, silicon carbide, titania, zirconia and magnesia. A carrier containing α-alumina as a primary component is particularly suitable. Further, the porous carrier may also contain a silica component with an upper limit usually set to about 10%.

In this invention, physical properties of the porous carrier may greatly affect the catalyst activity. The porous carrier usually has a surface area of 0.1–10 $m^2/g$, preferably 0.6–5 $m^2/g$, more preferably 0.8–2 $m^2/g$. To facilitate the operation of impregnating the catalyst components while maintaining such a surface area, the water absorbance of the carrier is preferably in a range of 20–50 %, more preferably 25–45 %.

Catalyst Composition

The catalyst of this invention contains silver preferably in an amount of 5–30 % by weight, more preferably 8–20% by weight, based on the total weight of the catalyst.

Besides silver, the catalyst of this invention also contains lithium and cesium as essential components. The respective contents of lithium and cesium in the catalyst are preferably in a range of 100–2000 ppm and 250–2000 ppm, more preferably 200–1000 ppm and 300–1600 ppm, based on the total weight of the catalyst. If the contents are outside the respective ranges, it would be difficult to obtain effect as a catalyst sufficiently superior to the conventional silver catalysts. The content ratio (Li/Cs) of lithium to cesium by weight is preferably in a range of 0.05:1–8:1, more preferably 0.1:1–4:1.

Further, the catalyst of this invention does not exclude alkaline metal components other than lithium and cesium. So long as the features of the catalyst of this invention are not impaired, the catalyst may contain sodium, potassium, rubidium, etc., as metal atoms usually in a range of about 10–10000 ppm.

In addition, so long as the features of the catalyst of this invention are not impaired, the catalyst may further contain other components acting as a promoter usually in a range of about 10–10000 ppm. These components include, for example, alkaline-earth metals such as beryllium, calcium, strontium, barium and magnesium, metals of Group 11 such as copper and gold, metals of Group 12 such as zinc, cadmium and mercury, metals of Group 13 such as boron, gallium, indium and thallium, metals of Group 14 such as germanium, tin and lead, metals of Group 15 such as phosphorus, arsenic, antimony and bismuth, metals of Group 4 such as titanium, zirconium and hafnium, metals of Group 5 such as silicon, vanadium, niobium and tantalum, metals of Group 6 such as chromium, molybdenum and tungsten, metals of Group 7 such as rhenium, and rare earth metals such as scandium, yttrium, samarium, cerium, lanthanum, neodymium, praseodymium and europium. The above optional components may be deposited on the carrier in either the pretreating step and the main treating step for preparation of the catalyst described later, but are preferably impregnated in the carrier at the same time as silver in the main treating step.

Preparation of Catalyst, Pretreating Step

The catalyst of this invention is prepared by pretreating a porous carrier with a solution containing a lithium compound and a cesium compound, thereafter, impregnating a solution containing a silver compound and a cesium compound in the pretreated porous carrier and then heat-treating the impregnated porous carrier. The subsequent description will be made by defining, as "pretreating step", the former step of pretreating a porous carrier with a solution containing a lithium compound and a cesium compound, and as "main treating step", the latter step of impregnating a solution containing a silver compound and a cesium compound in the pretreated porous carrier and then heat-treating the impregnated porous carrier.

In the pretreating step of this invention, lithium and cesium are deposited on the porous carrier by impregnating a solution containing a lithium compound and a cesium compound in the porous carrier and then drying the porous carrier by heat treatment. The lithium compound and cesium compound can be impregnated by, for example, a method of immersing the porous carrier in the solution containing the lithium compound and cesium compound, or a method of spraying the solution containing the lithium compound to the porous carrier. The heat treatment can be performed after the impregnation by, for example, separating the porous carrier and a surplus of the solution containing the lithium compound and cesium compound from each other, and then drying the porous carrier under reduced pressure or heating. Alternatively, the treatment with the solution containing the lithium compound and the treatment with the solution containing the cesium compound may be separately carried out. It is desired that the heat treatment be performed by using inert gas such as air and nitrogen or superheated steam preferably in a temperature range of 100–300 τ, more preferably 130–200 τ. Particularly desirable is a method using superheated steam.

The lithium compound used in the pretreating step of this invention is not subject to any special limitations. However, as the lithium component once deposited on the carrier should be less likely to elute again during the main treating step, it is desirable for the lithium compound to have relatively low solubility to water. From this viewpoint, preferable examples of the lithium compound are lithium carbonate, lithium bicarbonate, and carboxylates of lithium such as lithium oxalate and lithium acetate. Of these examples, lithium carbonate and lithium bicarbonate are particularly preferable. Further, a solvent can be employed without any special limitations so long as it is inactive against and has high solubility to the lithium compound used. Examples of the solvent include organic solvents having a low boiling point, and water.

The cesium compound used is not subject to any special limitations regarding type. For example, nitrates, hydroxides, halides, carbonates, bicarbonates and carboxylates of cesium can be used. From a handling stand point, it is preferable to employ the same anion salt as the lithium compound employed simultaneously. Therefore, carbonates, bicarbonates and carboxylates of cesium are preferable.

When employing that process, the cesium compound is impregnated and heat-treated at the same time as the lithium compound in the pretreating step preferably in an amount of 5–95%, more preferably 10–80%, based on the total amount of cesium to be impregnated, so that cesium is deposited along with lithium on the carrier. Accordingly, the content of cesium deposited on the carrier in the pretreating step is preferably in a range of 50–1800 ppm, more preferably 75–1375 ppm. Note that the amount of cesium deposited in the pretreating step should be not too much, because if it is too much, resulting in a lowering of activity and selectivity.

A catalyst having higher selectivity can be obtained by only using the main treating step according to the present invention in comparison with a process of impregnating the total lithium and cesium is preferable in that the total amount of cesium required to provide the catalyst having comparable selectivity is about 5–50 % less than required by another process of impregnating all of the cesium in the main treating step described later.

Preparation of Catalyst, Main Treating Step

The main treating step is a step in which a solution containing a silver compound and a cesium compound is impregnated in the porous carrier on which lithium and cesium have been deposited in the above-stated pretreating step, and heat treatment is performed on the impregnated porous carrier.

The silver compound advantageously used to deposit silver on the carrier in the main treating step is one which forms a complex soluble in a solvent with an amine compound, for example, and which decomposes at temperatures not higher than 500 τ, preferably not higher than 300 τ, more preferably not higher than 260 τ, and precipitates silver. Examples of the silver compound advantageously used include silver oxide, silver nitrate, silver carbonate, and various silver carboxylates such as silver acetate and silver oxalate. Above all, silver oxalate is particularly preferable. The amine compound as a complex forming agent is selected to make the silver compound in the solvent. Examples of the amine compound are pyridine, acetonitrile, ammonia, and amines having 1–6 carbon atoms. Of these examples, ammonia, pyridine, monoamines such as butyl amine, alkanolamines such as ethanolamine, and polyamines such as ethylenediamine and 1,3-propane diamine are preferable. Above all, the use of ethylenediamine and/or 1,3-propane-diamine, particularly, the combined use of them, is optimum.

As a process of impregnating the silver compound, it is most realistic to employ the silver compound in the form of an aqueous solution with the amine compound, but an aqueous solution added with alcohol, etc. may also be used. The silver concentration in an impregnating solution is determined so that silver of 5–30% by weight is finally deposited as a catalyst component. After the impregnation, if necessary, pressure reduction, heating, spraying, etc., can also be performed. Amine is added in an amount required to form a complex with the silver compound (usually two amino groups correspond to one silver atom). In this connection, it is preferable from the reactivity point of view that the amine compound be added 5–30% in excess of the above required amount.

The cesium compound used in the main treating step can be the same as described above in connection with the pretreating step. The cesium compound is dissolved in the aqueous solution of the silver compound and deposited on the carrier at the same time as silver. The content of cesium deposited on the carrier in the main treating step is preferably in a range of 200–2000 ppm, more preferably 225–1525 ppm. If the amount of cesium deposited in the main treating step is less than 200 ppm, selectivity would be deteriorated.

Conversely, if it is more than 2000 (i.e., the total cesium content is too much), activity and selectivity would both be deteriorated.

While impregnating the lithium compound in the pretreating step is one feature of this invention, this feature does not exclude that part of the lithium compound may be impregnated in the main treating step.

The heat treatment after the impregnation is carried out while measuring the temperature and time required for silver to precipitate on the carrier. It is most preferable to select the conditions of precipitation so that silver is present in as uniform a distribution as possible on the carrier in the form of fine particles. Generally, as the temperature and time of heat treatment increases, the treatment result becomes less satisfactory because aggregation of the precipitated silver particles is promoted correspondingly. The preferable heat treatment is performed at 130 τ–300 τ for a short time of from 5 minutes to 30 minutes by using heated air (or inert gas such as nitrogen) or superheated steam. Such a heat treatment is also desirable from the viewpoint of cutting down the time required for preparation of the catalyst. Further, the use of superheated steam is particularly desirable in order to make the silver distribution on the carrier more uniform and to improve the performance of the catalyst.

Reaction Process

The reaction for converting ethylene into ethylene oxide with the catalyst of this invention can be performed in a conventional manner. The reaction pressure is usually in a range of 0.1–3.6 MPa (0–35 kg/cm$^2$G) and the reaction temperature is usually in a range of 180–350 τ, preferably 200–300 τ. Generally used as the reaction material gas is a gas mixture consisting of 1–40 % by volume ethylene and 1–20% by volume molecular oxygen. Also, a diluent, e.g., an inert gas such as methane and nitrogen, can be generally mixed at a certain proportion, e.g., in a range of 1–70% by volume. As the gas containing molecular oxygen, air or oxygen for industrial purposes is usually employed. Further, a reaction modifier, e.g., hydrocarbon halide, in an amount of about 0.1–50 ppm can be added to the reaction material gas. The addition of a reaction modifier is effective to prevent hot spots from being formed in the catalyst and to greatly improve the performance of the catalyst, especially selectivity of the catalyst.

EXAMPLES

This invention will hereinafter be described in more detail with reference to embodiments, but this invention is not limited to these embodiments. The physical properties of carriers used in the following Examples and Comparative Examples are listed in Table 1 below.

TABLE 1

| Carrier | Surface area (m$^2$/g) | Water absorbance (%) | Average porous size (μm) | Silica content (%) |
|---|---|---|---|---|
| A | 1.04 | 32.3 | 1.4 | 3.0 |
| B | 1.05 | 36.3 | 1.5 | 0.07 |
| C | 1.11 | 40.6 | 1.2 | 0.42 |
| D | 0.93 | 28.0 | 1.2 | 1.3 |
| E | 1.09 | 42.8 | 1.2 | 5.9 |
| F | 1.20 | 35.9 | 1.5 | 6.0 |
| G | 1.55 | 34.1 | 1.1 | 2.6 |
| H | 1.55 | 33.8 | 1.1 | 6.0 |
| I | 1.49 | 34.8 | 1.2 | 2.6 |

Example 1

(1) Pretreatment of Carrier 50 g of an α-alumina carrier A (surface area 1.04 m$^2$/g; water absorbance 32.3%; average diameter of pores 1.4 μm; silica content 3%; ring-like shape with a size of 8ϕ×3ϕ×8 mm) was immersed in 100 ml of aqueous solution in which 0.94 g of lithium carbonate (Li$_2$CO$_3$) and 0.087 g of cesium carbonate (Cs$_2$CO$_3$) were dissolved. After removing surplus the solution, the carrier was heated with superheated steam of 150 τ for 15 minutes at a flow speed of 2 m/sec. A carrier impregnated with lithium and cesium components was thereby prepared.

(2) Preparation of Silver Oxalate 228 g of silver nitrate (AgNO$_3$) and 135 g of potassium oxalate (K$_2$C$_2$O$_4$·H$_2$O) were each dissolved in 1 liter of water separately. The solutions were gradually mixed, while being heated at 60 τ, to obtain a white precipitate of silver oxalate. After filtration, the precipitate was washed with distilled water.

(3) Preparation of Silver-Amine Complex Solution

A part (12.3 g) of the silver oxalate (AgC$_2$O$_4$, water content of 19.47%) obtained in (2) was dissolved little by little in an amine mixed aqueous solution consisting of 3.42 g of ethylenediamine, 0.94 g of propanediamine and 4.54 g of water to prepare a silver-amine complex solution. The silver-amine complex solution was then mixed with 1 ml of aqueous solution containing 1.14% by weight of cesium chloride (CsCl) and 1.98% by weight of cesium nitrate (CsNO$_3$) while the mixture was being agitated. Then, 1 ml of aqueous solution containing 0.66% by weight of barium hydroxide 8 hydrates (Ba(OH)$_2$·8H$_2$O) was added to the above mixture.

(4) Preparation of Silver Catalyst 50 g of the α-alumina carrier impregnated with lithium and cesium, prepared in (1), was immersed in the silver-amine complex solution containing cesium and barium, prepared in (3) to perform the impregnation in an evaporator under reduced pressure and heating to 40 τ. The thus-impregnated carrier was heated with superheated steam of 200 τ for 15 minutes at a flow speed of 2 m/sec, thereby preparing a catalyst. The amounts of silver (Ag), cesium (Cs), lithium (Li) and barium (Ba) deposited on the catalyst were 12%, 595 ppm, 500 ppm and 50 ppm, respectively.

(5) Oxidizing Reaction of Ethylene

The catalyst prepared by the above process was crushed to a size of 6–10 mesh, and 3 ml of it was filled in a SUS-made reaction tube having an inside diameter of 7.5 mm. A reaction gas (composed of 30% of ethylene, 8.5% of oxygen, 1.5 ppm vinyl chloride, 6.0% of carbon dioxide and the remainder being nitrogen gas) was passed through the reaction tube under a pressure of 0.8 MPa (7 kg/cm$^2$G) at a GHSV of 4300 hr$^{-1}$. The reaction temperature T$_{40}$ at the time when the conversion of oxygen was 40% after one week from start of the reaction and the selectivity S$_{40}$ (%) of ethylene oxide based on ethylene at the time when the conversion of oxygen was 40 % are shown in Table 2.

Example 2

A catalyst was prepared and subjected to the reaction by the same process as in Example 1 except that the amount of lithium carbonate impregnated in the pretreating step was changed so that the amount of lithium deposited was 300 ppm. The reaction results are shown in Table 2.

Example 3

A catalyst was prepared and subjected to the reaction by the same process as in Example 1 except that the amount of lithium carbonate impregnated in the pretreating step was changed so that the amount of lithium deposited was 700 ppm. The reaction results are shown in Table 2.

Examples 4 and 5

Catalysts were prepared and subjected to the reaction by the same process as in Example 1 except that the amounts of cesium deposited respectively in the pretreating step and the main treating step were changed as shown in Table 2. The reaction results are shown in Table 2.

Comparative Examples 1 and 2

Catalysts were prepared and subjected to the reaction by the same process as in Example 1 except that lithium was not deposited on the carrier, cesium was not deposited in the pretreating step, and the amounts of cesium deposited respectively in the main treating step were changed as shown in Table 2. The reaction results are shown in Table 2.

Comparative Example 3

A catalyst was prepared and subjected to the reaction by the same process as in Comparative Example 1 except that the amounts of cesium deposited respectively in the pretreating step and the main treating step were changed as shown in Table 2. The reaction results are shown in Table 2.

Comparative Example 4

A catalyst was prepared and subjected to the reaction by the same process as in Comparative Example 1 except that lithium nitrate was impregnated in the main treating step so that the amount of lithium deposited was 500 ppm. The reaction results are shown in Table 2. Incidentally, it was tried to use lithium carbonate instead of lithium nitrate, but solubility of lithium carbonate into the sliver-amine complex solution was low and lithium could not be deposited in an amount as much as 500 ppm.

Comparative Example 5

A catalyst was prepared and subjected to the reaction by the same process as in Comparative Example 3 except that lithium nitrate was impregnated in the main treating step so that the amount of lithium atoms deposited was 500 ppm. The reaction results are shown in Table 2.

TABLE 2

| | Amount of Lithium deposited (ppm) | | Amount of Cesium deposited (ppm) | | | |
|---|---|---|---|---|---|---|
| | pre-treating step | main treating step | pre-treating step | main treating step | $T_{40}$ (°C.) | $S_{40}$ (%) |
| Example | | | | | | |
| 1 | 500 | 0 | 200 | 395 | 229.3 | 81.6 |
| 2 | 300 | 0 | 200 | 395 | 229.1 | 81.5 |
| 3 | 700 | 0 | 200 | 395 | 228.1 | 81.6 |
| 4 | 500 | 0 | 100 | 632 | 236.1 | 81.6 |
| 5 | 500 | 0 | 300 | 316 | 227.0 | 81.7 |
| Comparative Example | | | | | | |
| 1 | 0 | 0 | 0 | 595 | 235.0 | 80.5 |
| 2 | 0 | 0 | 0 | 395 | 224.0 | 78.4 |
| 3 | 0 | 0 | 200 | 395 | 240.2 | 81.1 |
| 4 | 0 | 500 | 0 | 595 | 247.1 | 80.4 |
| 5 | 0 | 500 | 200 | 395 | 244.4 | 78.1 |

Examples 6–16

Catalysts were prepared and subjected to the reaction by the same process as in Example 1 except that the kind of carrier, the step of impregnating cesium, and the amount of cesium deposited were changed as shown in Table 3. The reaction results are shown in Table 3.

TABLE 3

| | | Amount of Lithium deposited (ppm) | | Amount of Cesium deposited (ppm) | | | |
|---|---|---|---|---|---|---|---|
| Example | Carrier | pre-treating step | main treating step | pre-treating step | main treating step | $T_{40}$ (°C.) | $S_{40}$ (%) |
| 6 | B | 500 | 0 | 100 | 395 | 225.9 | 81.3 |
| 7 | C | 500 | 0 | 100 | 395 | 225.7 | 81.6 |
| 8 | D | 500 | 0 | 100 | 395 | 231.8 | 81.4 |
| 9 | E | 500 | 0 | 200 | 395 | 230.4 | 81.5 |
| 10 | F | 500 | 0 | 300 | 395 | 227.9 | 81.5 |
| 11 | G | 500 | 0 | 200 | 552 | 222.0 | 81.8 |
| 12 | G | 500 | 0 | 200 | 710 | 227.2 | 81.9 |
| 13 | G | 500 | 0 | 300 | 474 | 223.6 | 81.9 |
| 14 | G | 500 | 0 | 300 | 631 | 229.0 | 81.8 |
| 15 | H | 500 | 0 | 200 | 552 | 214.8 | 81.4 |
| 16 | H | 500 | 0 | 200 | 715 | 229.1 | 81.4 |

Example 17

A catalyst was prepared and subjected to the reaction by the same process as in Example 1 except that the step of impregnating cesium and the amount of cesium deposited were changed as shown in Table 4, and ammonium perrhenate was further added to the silver-amine complex solution. The amounts of silver (Ag), cesium (Cs), lithium (Li) and rhenium (Re) deposited on the catalyst were 12%, 870 ppm, 500 ppm and 370 ppm, respectively. The reaction results are shown in Table 4.

With the catalyst of this Example 18, the reaction temperature $T_{40}$ is increased due to addition of the rhenium component, while the selectivity ($S_{40}$) is remarkably improved.

Example 18

A catalyst was prepared and subjected to the reaction by the same process as in Example 1 except that a carrier I was used instead of the carrier A and predetermined amounts of cesium nitrate ($CsNO_3$), lithium tungstate ($Li_2WO_4$) and lithium nitrate ($LiNO_3$) were added to the silver-amine complex solution used in the main treating step. The amounts of Ag, Cs, W and Li deposited on the catalyst were 20%, 937 ppm, 468 ppm and 667 ppm, respectively. The reaction results are shown in Table 4.

TABLE 4

| | | Amount of Lithium deposited (ppm) | | Amount of Cesium deposited (ppm) | | | |
|---|---|---|---|---|---|---|---|
| Example | Carrier | pre-treating step | main treating step | pre-treating step | main treating step | $T_{40}$ (°C.) | $S_{40}$ (%) |
| 17 | A | 500 | 0 | 200 | 670 | 256.0 | 87.9 |
| 18 | I | 455 | 212 | 91 | 846 | 226.1 | 82.7 |

As described above, by employing the catalyst of this invention, ethylene oxide can be produced with higher selectivity and under more moderate conditions than is the case when employing conventional catalysts.

What is claimed is:

1. A catalyst for oxidizing ethylene and producing ethylene oxide, said catalyst being prepared by pretreating a porous carrier with a solution containing a lithium compound and a cesium compound, thereafter, impregnating a solution containing a silver compound and a cesium compound in the pretreated porous carrier and then heat-treating the impregnated porous carrier.

2. A catalyst according to claim 1, wherein said catalyst contains silver of 5 to 30% by weight.

3. A catalyst according to claim 1, wherein said catalyst contains lithium of 100 to 2000 ppm and cesium of 250 to 2000 ppm.

4. A catalyst according to claim 1, wherein a weight ratio (Li/Cs) of lithium to cesium is in a range of 0.1:1 to 4:1.

5. A catalyst according to claim 1, wherein 10 to 80% of the total cesium to be impregnated in said porous carrier is impregnated at the same time as said lithium compound.

6. A catalyst according to claim 1, wherein said carrier has a surface area in a range of 0.6 to 5 $m^2/g$.

7. A catalyst according to claim 1, wherein a main component of said carrier is α-alumina.

8. A catalyst according to claim 1, wherein said lithium compound is lithium carbonate or lithium bicarbonate.

9. A catalyst according to claim 1, wherein said lithium compound is lithium carboxylate.

10. A catalyst according to claim 1, wherein said pretreatment comprises the steps of impregnating a solution containing a lithium compound and a cesium compound in said porous carrier and then heat-treating the impregnated porous carrier.

11. A catalyst according to claim 10, wherein superheated steam is employed to perform the heat treatment in said pretreatment.

12. A catalyst according to claim 1, wherein said silver compound and said cesium compound are both impregnated by using an aqueous solution containing a silver compound, a cesium compound, and amine as a complex forming agent.

13. A catalyst according to claim 1, wherein superheated steam is employed to perform said step of impregnating a silver compound and a cesium compound in the porous carrier and then heat-treating the impregnated porous carrier.

14. A process for producing ethylene oxide wherein ethylene is subjected to vapor contact oxidation with molecular oxygen in the presence of the catalyst according to any of claims 1 to 13.

* * * * *